United States Patent [19]

Dewing

[11] Patent Number: 5,170,938

[45] Date of Patent: Dec. 15, 1992

[54] DEODORANT DEVICE FOR A ROLL ABSORBENT MATERIAL DISPENSER

[76] Inventor: Ronald Dewing, 794 Blackthorn Ave., El Cajon, Calif. 92020

[21] Appl. No.: 733,882

[22] Filed: Jul. 22, 1991

[51] Int. Cl.⁵ .................... A61L 9/00; A47K 10/16
[52] U.S. Cl. ............................ 239/52; 239/34; 242/55.55
[58] Field of Search ............. 239/34, 52; 242/55.55

[56] References Cited

U.S. PATENT DOCUMENTS

| | | | |
|---|---|---|---|
| 649,062 | 5/1900 | Levett | 242/55.55 |
| 2,728,604 | 12/1955 | Garfield | 242/55.55 |
| 2,988,283 | 6/1961 | Garfield | 242/55.55 |
| 3,771,883 | 11/1973 | Terepin | 242/55.55 |
| 4,565,336 | 1/1986 | Hefty et al. | 242/55.55 |

FOREIGN PATENT DOCUMENTS 232141 8/1987 European Pat. Off. .......... 242/55.55

Primary Examiner—Andres Kashnikow
Assistant Examiner—Karen B. Merritt
Attorney, Agent, or Firm—Frank D. Gilliam

[57] ABSTRACT

A decorative disk for attachment to the ends of a roll of absorbent paper material such as toilet tissue, paper towels or the like which is impregnated in the material of construction or coated with a pleasant odoriferous smelling material such as a perfume base for the purpose of deodorizing, providing a pleasant smell or the like to an area. The disk is generally constructed of a plastic material of a selected color. The disk has a hub area which is segmented for insertion into the bore of the hollow core of the roll of absorbent material with the disk portion closely adjacent and covering at least a portion of the outer roll surface. The distal surface of the disk portion being positioned adjacent to one end of the support for the roll of material on which it is attached. A disk is used preferably attached to both ends of the roll of absorbent material when used.

9 Claims, 1 Drawing Sheet

DEODORANT DEVICE FOR A ROLL ABSORBENT MATERIAL DISPENSER

BACKGROUND OF THE INVENTION

This invention relates to roll paper dispensers and more particularly to a deodorizing disk with a perfume base of a selected scent impregnated within the material of construction for insertion into the hollow central core or tube of a roll of absorbent material such as toilet paper, paper towels or the like. The roll support means holds the deodorizing disk in place while it turns with the dispensing of material from the roll.

U.S. Pat. Nos. 2,728,604 issued to I. W. Garfield; 2,806,738 issued to J. Tsakalas; and 4,901,889 all teach deodorant material.

The three above noted Patents teach the containment of a deodorant material captive within the hollow spindle of the paper roll support mechanism with vent means allowing the scent from the deodorant to escape in a controlled manner to the exterior of the spindle for the purpose of deodorizing an area surrounding the device. None of these items are of a decorative nature and the dispensing mechanism is generally not visible to a viewer of the device.

There has not been a deodorant device that is pleasant to the eye of a viewer, convenient to use, inexpensive to manufacture and highly effective for deodorizing an area adjacent to the device until the emergence of the instant deodorizing device.

SUMMARY OF THE INVENTION

The deodorant device of the present invention has an exterior disk or wheel and a central hub. The material of construction, generally plastic is impregnated with a scent which provides a pleasant smell to the area therearound. The central hub extending in a direction normal to the disk or wheel and is configured to be insertable within the hollow of a core or spindle generally used as a carrier for the roll of absorbent material as for example, toilet paper, paper towels or the like. The hub is segmented, ie. has spaced apart resilient fingers which allow the hub to be inserted in to different diameter hollow portions of the core or spindle. The hub of the invention is designed to be insertable into one end of the hollow central portion of the core or spindle before the roll of absorbent material is mounted on a dispensing device for dispensing of the material from the roll. Generally one of the devices of the invention is inserted into each end of roll in a like manner.

In addition to the use of the device of the invention for the purpose of masking undesirable odors in the surrounding area, the device in addition can have advertising or display material positioned on the disk portion of the device which can either be molded therein or applied to the surface thereof.

An object of this invention is to provide a deodorizing device that is effective for the purpose intended.

Another object of this invention is to provide a decorative deodorizing device for rolls of absorbent material such as paper towels and toilet paper.

Still another object of this invention is to provide a deodorant dispensing device that has advertising display on the ends thereof.

Still another object of this invention is to provide a deodorant dispensing device for use with rolls of absorbent and the like material which is inexpensive to produce and is dispensable.

Other objects and features of the invention will become apparent as the drawings which follow are understood by reading the corresponding description thereof.

BRIEF DESCRIPTION OF THE DRAWING FIGURES

DETAILED DESCRIPTION OF THE PREFERRED EMBODIMENT

Figure 1:
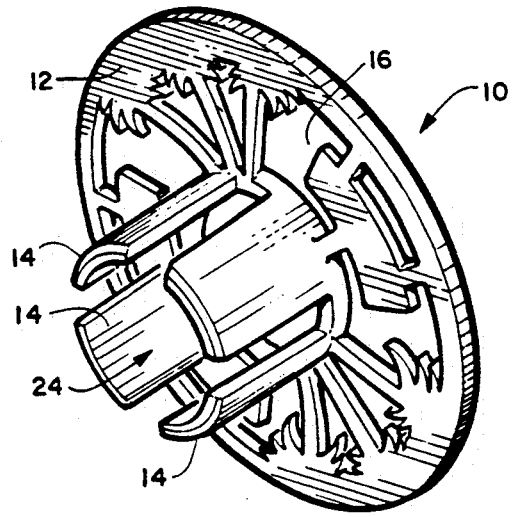
FIG. 1 is a perspective showing of a deodorant disk of the invention.

Referring now to the various drawing figures, FIG. 1 depicts an elevated perspective showing of the deodorant device 10 of the invention. The deodorant device 10 includes a large disk surface 12 with a plurality of designs embossed thereon or through the surface and the latter thereof having openings therethrough, displaying advertising indicia or the like. The diameter of the surface of disk 1 is generally equal to the maximum diameter of the roll of material to which is to be attached as herein after explained in greater detail.

A plurality of spaced apart tabs 14 extending normal to the surface of the disk 12 for insertion into the hollow central core of a roll of disposable material such as toilet paper, paper towels or the like are utilized to attach the deodorant disk to the roll of material.

The deodorant device 10 is impregnated with a concentration of a selected perfume base having a pleasant odor which emits from and permeates the immediate area around the deodorant disk 10 masking any unpleasant odors in the immediate area thereof. The perfume base is added to the materials used for the making of the plastic from which the deodorant disk is constructed. The addition of a perfume base is well known in the plastic art and does not form a part of this invention. The addition of a perfume base to the formation of plastic has been used for many years to add a concentrated perfume base to plastic ladies ear rings.

The deodorant device of this invention can be formed by any known plastic forming method such as, but not limited to, injection molding, casting or the like. Injection molding is the preferable method.

Figure 2:
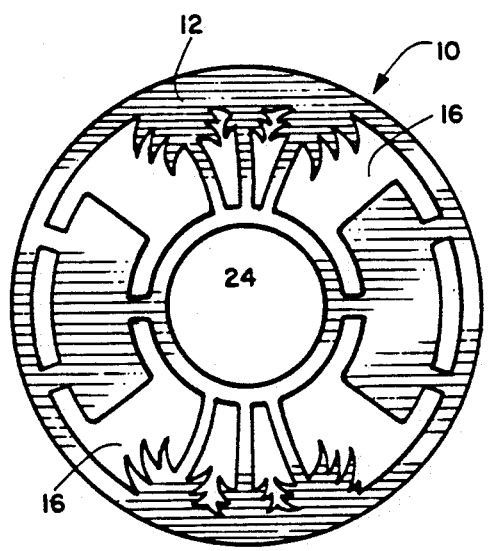
FIG. 2 is a plan view showing the outer normally exposed surface of the deodorant disk of the invention.

Drawing FIG. 2 depicts a plan view of the distal or exposed side of the deodorant device 10 of the invention showing openings 16 therethrough formed by indicia thereof.

Figure 3:
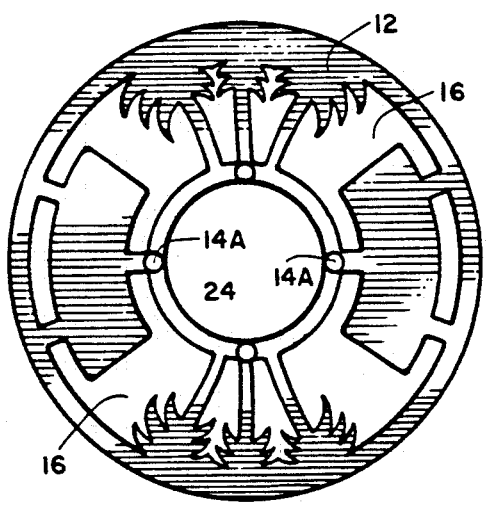
FIG. 3 is a plan view showing the normally non-exposed surface of the deodorant disk of the invention.

Drawing FIG. 3 depicts a plan view of the normally concealed side of the disk 12 of the deodorant device 10 of the invention showing the location of the extended tabs 14A. It should be noted that the tabs 14 may either have considerable width as seen in drawing FIG. 1 or be in the form of small round pegs 14A. The resiliency of the tabs 14 is dictated by their width. The material of construction and the width of the tabs are selected so that they can be inserted within the ends of hollow central cores, as discussed herein, of a variety of slightly different diameters of hollow central core portions 15 as seen in drawing FIG. 4.

Figure 4:
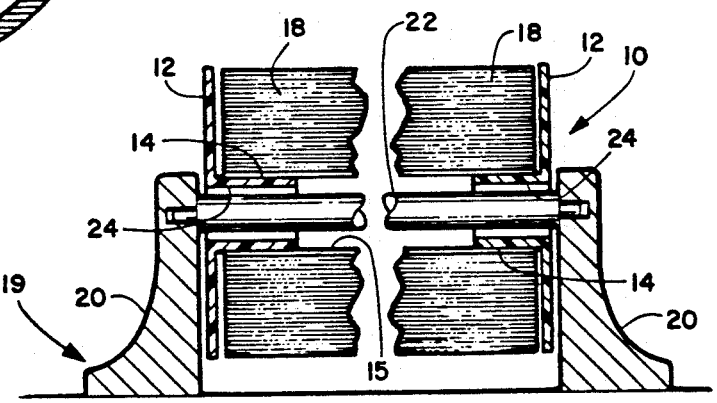
FIG. 4 is a perspective showing of a pair of deodorant disks of the invention inserted in operating position on a roll of absorbent material ready for dispensing.

Drawing FIG. 4 depicts an elevated perspective showing of the deodorant device of the invention installed on a roll of dispensable material 18 that is shown supported by a dispensing mechanism 19 comprising a pair of two spaced apart mounting brackets 20 which are attached to a fixed supporting surface, not shown.

The deodorant device of the invention is first inserted into the end of the hollow central core of the roll of material to be dispensed and then onto the roll supporting portions of the mounting brackets 20 of the dispensing device which passes through opening 24 of the deodorant device 10. If the dispensing device includes a roller bar 22 then the roller bar is inserted through the opening 24 of the deodorant device 10.

Although the deodorant device of this invention is described as being constructed of plastic material it should be understood that type of material suitable for the purpose described and intended can be used in the construction of the deodorant device.

It should be further understood that the deodorant device 10 of the invention may be used on the ends of a roll of any type dispensable material with an open or hollow central core like those found in the toilet paper and paper towel dispensing art.

While specific embodiments of the deodorant disk has been shown and fully explained above for the purpose of illustration it should be understood that many alterations, modifications and substitutions may be made to the instant invention disclosure without departing from the spirit and scope of the invention as defined by the appended claims.

What is claimed is:

1. A deodorant device for removable attachment to a roll of material to be dispensed for masking the smell of unpleasant odors in adjacent areas thereto, said roll including a hollow central core having ends normally used for mounting said roll on a mechanism for dispensing therefrom by rotating the roll while dispensing material comprising:

a disk member having a diameter substantially the same as the maximum expected diameter of said roll of material to be dispensed;

attachment means for attaching said deodorant device to one of said ends of said central core;

a selected concentrated perfume base carried by at least said disk member whereby the odor from said concentrated perfume base permeates the area of said device pleasantly masking any obnoxious odors in that immediate area.

2. The deodorant device of claim 1, wherein said disk member has at least a central opening therethrough.

3. The deodorant device of claim 1 wherein said attachment means comprises spaced apart tabs extending from said disk member and in a direction normal thereto for insertion within one of said ends of said central core.

4. The deodorant device as defined in claim 3 wherein said spaced apart tabs have widths that allow sufficient resiliency to conform to various diameters of said hollow central core.

5. The deodorant device of claim 1 wherein at least said disk member is impregnated with said perfume base.

6. The deodorant device of claim 5 wherein both said disk member and said attachment means are impregnated with said perfume base.

7. The deodorant device of claim 1 wherein said deodorant device is constructed of a plastic material.

8. The deodorant device of claim 1 wherein said disk member and said attachment means are an integral unit.

9. The deodorant device of claim 8 wherein said perfume base is carried by both said disk member and attachment means.

* * * * *